US 9,500,597 B2

(12) United States Patent
Guan

(10) Patent No.: US 9,500,597 B2
(45) Date of Patent: Nov. 22, 2016

(54) DETERMINATION OF ABSOLUTE DIMENSIONS OF PARTICLES USED AS CALIBRATION STANDARDS FOR OPTICAL MEASUREMENT SYSTEM

(75) Inventor: Yu Guan, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/524,147

(22) Filed: Jun. 15, 2012

(65) Prior Publication Data

US 2013/0003053 A1    Jan. 3, 2013

Related U.S. Application Data

(60) Provisional application No. 61/502,489, filed on Jun. 29, 2011.

(51) Int. Cl.
| | | |
|---|---|---|
| *G01N 15/02* | (2006.01) | |
| *G01N 21/93* | (2006.01) | |
| *G01N 21/95* | (2006.01) | |
| *G01N 21/956* | (2006.01) | |

(52) U.S. Cl.
CPC .......... *G01N 21/93* (2013.01); *G01N 21/9501* (2013.01); *G01N 21/956* (2013.01)

(58) Field of Classification Search
CPC ...... G01N 21/84; G01N 21/88; G01N 23/20; G06F 15/00
USPC ............... 356/335, 243.6; 702/166; 429/219; 378/73
See application file for complete search history.

(56) References Cited

U.S. PATENT DOCUMENTS

| | | | |
|---|---|---|---|
| 4,821,302 A * | 4/1989 | Whitlock et al. | 378/73 |
| 7,027,146 B1 * | 4/2006 | Smith et al. | 356/243.6 |
| 2011/0159368 A1 * | 6/2011 | Hirose et al. | 429/219 |
| 2012/0016630 A1 * | 1/2012 | Shintani et al. | 702/166 |

FOREIGN PATENT DOCUMENTS

| | | |
|---|---|---|
| CN | 102110853 A | 6/2011 |
| EP | 1475242 | 11/2004 |
| JP | 59037444 | 2/1984 |
| RU | 1775655 | 11/1992 |
| RU | 2007108198 | 9/2008 |
| WO | 2010109285 A1 | 9/2010 |

* cited by examiner

*Primary Examiner* — Tarifur Chowdhury
*Assistant Examiner* — Jamil Ahmed
(74) *Attorney, Agent, or Firm* — Suiter Swantz pc llo

(57) ABSTRACT

The present invention includes providing a plurality of standard particles; providing a substantially crystalline material having one or more characteristic spatial parameters, disposing the plurality of standard particles proximate to a portion of the substantially crystalline material, acquiring imagery data of the plurality of standard particles and the portion of the substantially crystalline material, establishing a spatial relationship between the plurality of standard particles and the portion of the substantially crystalline material utilizing the acquired imagery data, and determining one or more spatial parameters of the plurality of standard particles utilizing the one or more characteristic spatial parameters of the substantially crystalline material and the established spatial relationship between the plurality of standard particles and the portion of the substantially crystalline material.

25 Claims, 7 Drawing Sheets

DETERMINATION OF ABSOLUTE DIMENSIONS OF PARTICLES USED AS CALIBRATION STANDARDS FOR OPTICAL MEASUREMENT SYSTEM

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled Method of Accurate Determination of Absolute Dimensions of Nanoparticles Used as Calibration Standards for Optical Inspection Systems, naming Yu Guan as an inventor, filed Jun. 29, 2011, Application Ser. No. 61/502,489.

TECHNICAL FIELD

The present invention relates to the field of optical inspection systems, and in particular to system and method for acquiring spatial parameters for one or more standard particles utilized to calibrate an optical inspection system.

BACKGROUND

As performance demand on semiconductor devices continues to increase, specification requirements for the various features of semiconductor devices will continue to become more stringent. To meet this demand it is critical that future methods and systems for device fabrication and characterization are able to quantify device feature sizes at ever decreasing levels. In order to optically determine device feature sizes at very small dimensions implementing optical measurement systems, such as optical inspection systems and optical metrology systems, require calibration. One commonly utilized calibration technique includes the utilization of certified standardized particles to calibrate an implementing optical metrology system utilized to acquire imagery or other optical data of one or more device features or defects. However, standardized particles are typically only certified down to approximately 50-60 nm, with the smallest pitch standard being 100 nm. As a result, significant extrapolation must be used in order to quantify device features below this level. This extrapolation leads to uncertainties in measured sizes of features and is compounded at smaller and smaller sizes. Therefore, it would be advantageous to provide a system and method that cures the defects of the prior art allowing improved optical size characterization of semiconductor device features.

SUMMARY

A system for determining one or more spatial parameters of a plurality of standard particles is disclosed. The system includes, but is not limited to, a substantially crystalline material having one or more characteristic spatial parameters; a plurality of standard particles disposed proximate to a portion of the substantially crystalline material; a microscopy system configured to acquire imagery data of the plurality of standard particles and the portion of the substantially crystalline material; and a computing system communicatively coupled to the microscopy system, the computing system configured to establish a spatial relationship between the a plurality of standard particles and the portion of the substantially crystalline material, the computing system further configured to determine one or more spatial parameters of the a plurality of standard particles utilizing the one or more characteristic spatial parameters of the substantially crystalline material and the established spatial relationship between the plurality of standard particles and the portion of the substantially crystalline material.

In another aspect, the system may include, but is not limited to, a substantially crystalline material having one or more characteristic spatial parameters; one or more standard particles disposed proximate to a portion of the substantially crystalline material; a microscopy system configured to acquire imagery data of the one or more standard particles and the portion of the substantially crystalline material; and a computing system communicatively coupled to the microscopy system, the computing system configured to establish a spatial relationship between the one or more standard particles and the portion of the substantially crystalline material, the computing system further configured to determine one or more spatial parameters of the one or more standard particles utilizing the one or more characteristic spatial parameters of the substantially crystalline material and the established spatial relationship between the one or more standard particles and the portion of the substantially crystalline material.

A method for determining one or more spatial parameters of a plurality of standard particles is disclosed. The method may include, but is not limited to, providing a plurality of standard particles; providing a substantially crystalline material having one or more characteristic spatial parameters; disposing the plurality of standard particles proximate to a portion of the substantially crystalline material; acquiring imagery data of the plurality of standard particles and the portion of the substantially crystalline material; establishing a spatial relationship between the plurality of standard particles and the portion of the substantially crystalline material utilizing the acquired imagery data; and determining one or more spatial parameters of the plurality of standard particles utilizing the one or more characteristic spatial parameters of the substantially crystalline material and the established spatial relationship between the plurality of standard particles and the portion of the substantially crystalline material.

In another aspect, the method may include, but is not limited to, providing one or more standard particles; providing a substantially crystalline material having one or more characteristic spatial parameters; disposing the one or more standard particles proximate to a portion of the substantially crystalline material; acquiring imagery data of the one or more standard particles and the portion of the substantially crystalline material; establishing a spatial relationship between the one or more standard particles and the portion of the substantially crystalline material utilizing the acquired imagery data; and determining one or more spatial parameters of the one or more standard particles utilizing the one or more characteristic spatial parameters of the substantially crystalline material and the established spatial relationship between the one or more standard particles and the portion of the substantially crystalline material.

A method for calibrating an optical measurement system utilizing a plurality of standard particles is disclosed. The method may include, but is not limited to, providing a plurality of standard particles; providing a substantially crystalline material having one or more characteristic spatial parameters; disposing the plurality of standard particles proximate to a portion of the substantially crystalline material; acquiring imagery data of the plurality of standard particles and the portion of the substantially crystalline material; establishing a spatial relationship between the plurality of standard particles and the portion of the substantially crystalline material utilizing the acquired imagery data; determining one or more spatial parameters of the plurality of standard particles utilizing the one or more characteristic spatial parameters of the substantially crystalline material and the established spatial relationship between the plurality of standard particles and the portion of the substantially crystalline material; disposing the plurality of standard particles on a surface of a wafer; and calibrating an optical measurement system utilizing the wafer having the plurality of standard particles disposed on the surface of the wafer by: acquiring optical data associated with the plurality of standard particles disposed on the surface of the wafer; and establishing a relationship between the acquired optical data associated with the plurality of standard particles and the one or more spatial parameters of the plurality of standard particles.

A wafer for calibrating an optical measurement system is disclosed. The wafer may include, but is not limited to, a calibration wafer; and plurality of calibrated standard particles disposed on a surface of the wafer, each of the plurality of calibrated standard particles selected from a plurality of standard particles having one or more verified spatial parameters, the one or more verified spatial parameters confirmed utilizing a spatial comparison between one or more standard particles of the plurality of standard particles and a portion of a substantially crystalline material having one or more characteristic spatial parameters.

An optical measurement system configured to perform optical inspection or optical metrology on one or more wafers is disclosed. The system may include, but is not limited to, an illumination source configured to direct illumination to a surface of a sample disposed on a sample stage; a sample stage configured to receive a calibration wafer, the calibration wafer having a plurality of calibrated standard particles disposed on a surface of the calibration wafer, the plurality of calibrated standard particles selected from a plurality of standard particles having one or more verified spatial parameters, the one or more verified spatial parameters confirmed utilizing a spatial comparison between one or more standard particles of the plurality of standard particles and a portion of a substantially crystalline material having one or more characteristic spatial parameters; a detector configured to receive illumination from the surface of the sample; and a computing system communicatively coupled to the detector, the computing system configured to acquire information associated with illumination received by the detector, the computing system further configured to acquire data associated with the plurality of calibrated standard particles disposed on the surface of the calibration wafer utilizing information associated with illumination received by the detector, the computing system further configured to establish a relationship between the data acquired by the computing system about the plurality of calibrated standard particles disposed on the surface of the wafer and the one or more verified spatial parameters of the plurality of calibrated standard particles, wherein the computing system is further configured to calibrate subsequent measurements made by the inspection system utilizing the established relationship.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1A:
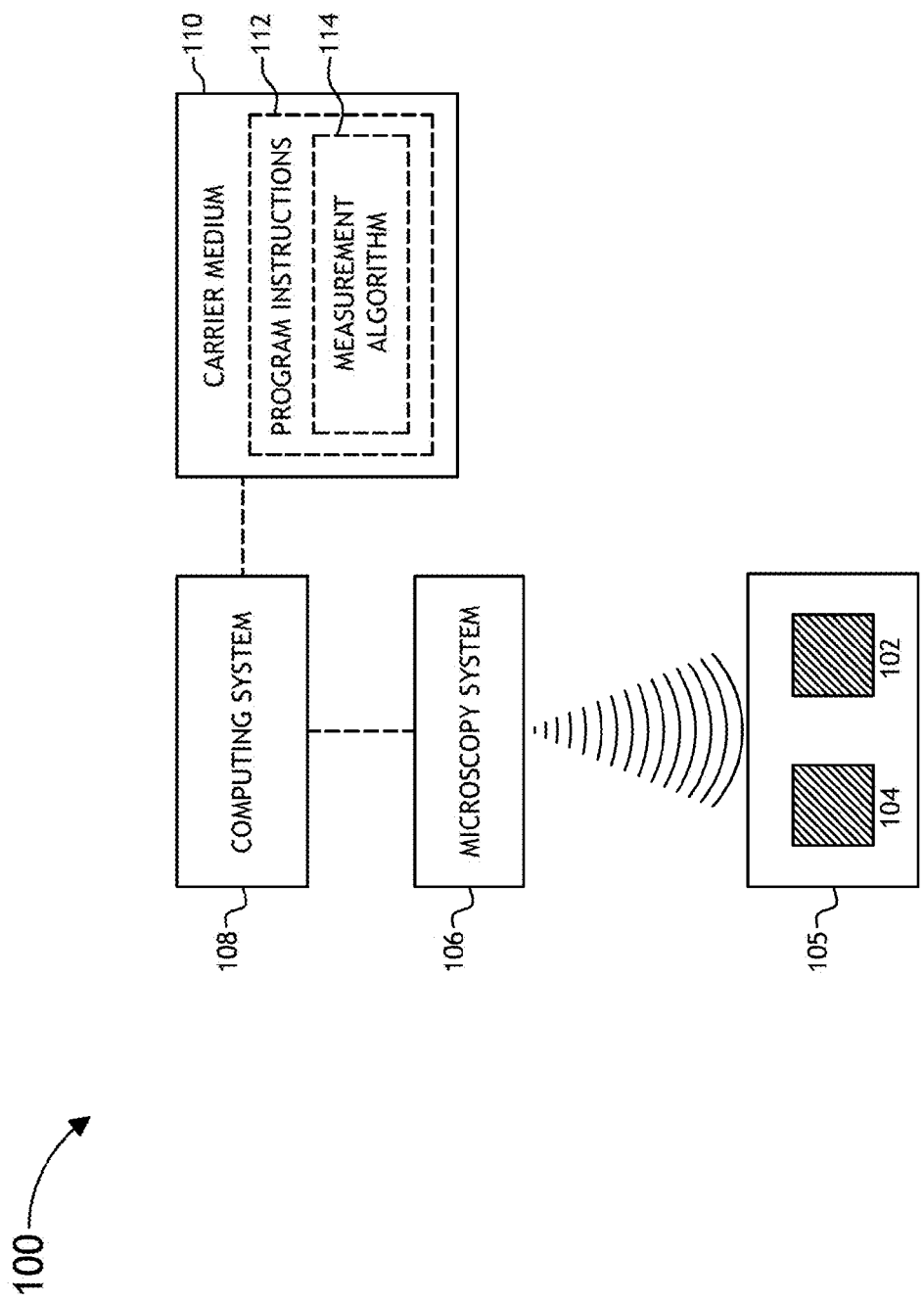
FIG. 1A is a block diagram illustrating a system for determining one or more spatial parameters of a plurality of standard particles, in accordance with one embodiment of the present invention.

Reference will now be made in detail to the subject matter disclosed, which is illustrated in the accompanying drawings.

Referring generally to FIGS. 1A through 5, systems and methods for determining spatial parameters (e.g. dimensions) of a plurality of standard particles for calibrating optical systems, such as an inspection system or metrology system, are described. Optical systems are commonly utilized for inspecting wafers prior to, during, and following fabrication of semiconductors. The size measurement accuracy of most optical systems is limited by spatial parameters of standard particles utilized for calibration. The present invention is directed towards a system and method for measuring one or more spatial parameters of a plurality of standard particles utilizing known or readily ascertainable characteristic spatial parameters of substantially crystalline materials. Utilizing spatial parameters of substantially crystalline materials, it is possible to determine spatial parameters of standard particles with a relatively high degree of accuracy and precision due to the resolution of crystal lattices within substantially crystalline materials and the substantially uniformity of crystal structures within such materials.

As used throughout the present disclosure, the term "standard particle" generally refers to any particle, material, object, or artifact having one or more characteristic spatial parameters (e.g. diameter, circumference, size, volume, length, width, thickness, height or any other substantially fixed dimension of set of dimensions). For example, a standard particle may include but are not limited to silica, silicon particles, polymer particles, and the like. Many different types of standard particles are known to the art, and the term standard particle as used herein is intended to encompass any particle, material, object, or artifact acceptable for calibrating an optical system.

As used throughout the present disclosure, the terms "substantially crystalline material" or "crystalline material" generally refer to a material having crystal structures with one or more substantially uniform or repetitious spatial parameters (e.g. lattice plane spacing, unit cell dimensions, unit cell configurations, etc.). For example, a substantially crystalline material may include gold, asbestos, silicon, another monocrystalline material known to the art, or any material having constituent atoms, molecules, or ions arranged in a substantially uniform or repeating pattern. Many different crystalline materials are known in the art, and the terms crystalline material or substantially crystalline material as used herein are intended to encompass any crystalline or substantially crystalline material having a crystalline structure with known or readily ascertainable characteristic spatial parameters.

As used throughout the present disclosure, the terms "sample" or "wafer" generally refer to any substrate formed of a semiconductor or non-semiconductor material. For example, semiconductor or non-semiconductor materials include, but are not limited to, quartz, monocrystalline silicon, gallium arsenide, and indium phosphide. A wafer may include one or more layers. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

Figure 1B:
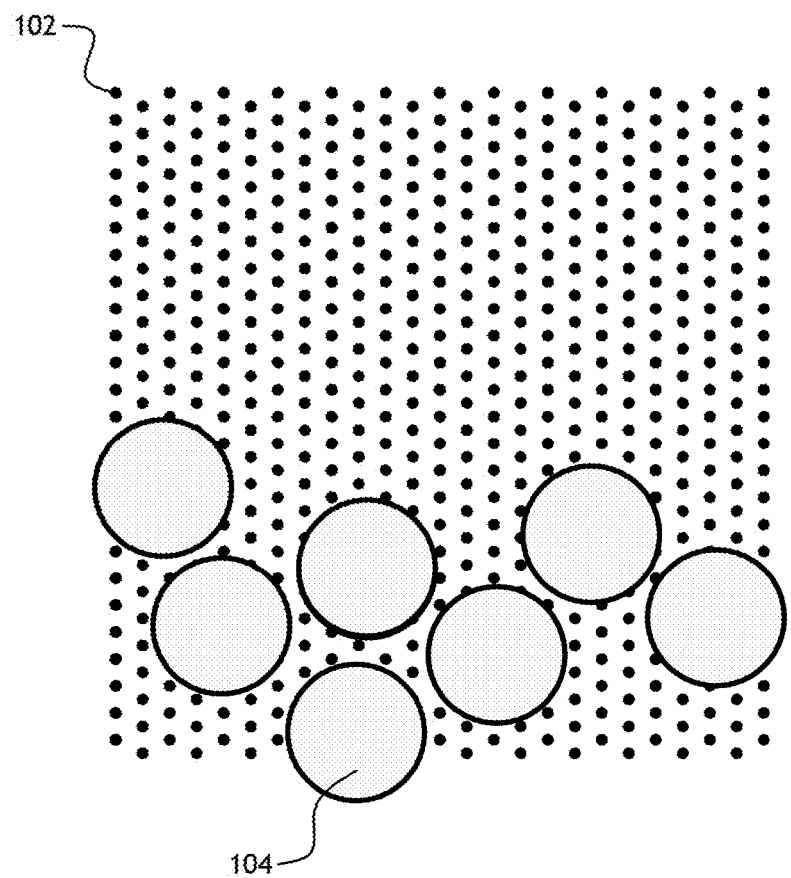
FIG. 1B illustrates a conceptual view of a plurality of standard particles disposed proximate to a substantially crystalline material, in accordance with one embodiment of the present invention.
Figure 1C:
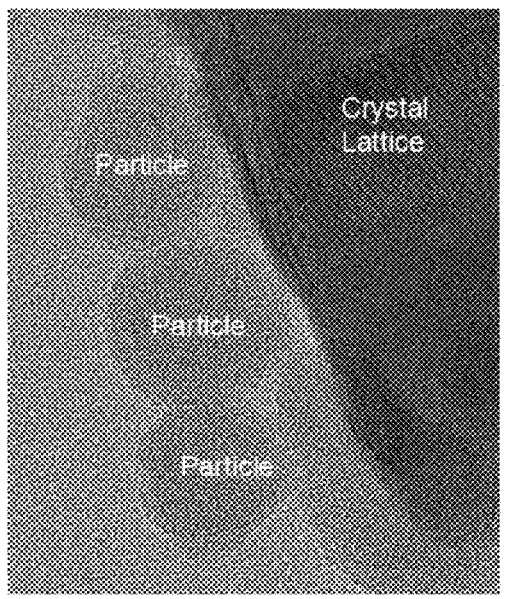
FIG. 1C is a TEM image of a plurality of standard particles disposed proximate to a substantially crystalline material, in accordance with one embodiment of the present invention.

FIGS. 1A through 1C illustrate a system 100 for determining one or more spatial parameters of standard particles 104, such as the diameter, circumference, size, volume, length, width, thickness, height or any other substantially fixed dimension of set of dimensions of the one or more standard particles 104. It is noted herein that in determining one or more spatial parameters associated with the standard particles 104, the system 100 may determine some statistical measure of the given parameter. For example, the system 100 may determine an average, mean, standard deviation and the like of one or more spatial parameters of the standard particles. For instance, the system 100 may determine an average size of the plurality of standard particles.

While the remainder of this disclosure describes the present invention in the context of determining one or more spatial parameters associated with a plurality of standard particles, it is noted herein that the present invention may be extended to the determination of one or more spatial parameters associated with a single particle. In this context, the system 100 may determine the diameter, circumference, size, volume, length, width, thickness, height or any other substantially fixed dimension of a single standard particle.

In one embodiment, the system 100 may include a sample stage 105 configured to receive the standard particles 104 and a substantially crystalline material 102 configured for spatial comparison with the standard particles 104. The substantially crystalline material may have one or more substantially uniform or repetitious characteristic spatial parameters (e.g. lattice plane spacing, unit cell dimensions, unit cell configurations, etc.).

Referring to FIGS. 1B and 1C, the one or more characteristic spatial parameters of the substantially crystalline material 102 may consist of one or more known values or may be readily ascertainable utilizing systems or methods known to those skilled in the art. For example, the one or more characteristic spatial parameters may include one or more lattice plane spacings, which define one or more unit cells of the substantially crystalline material 102. The one or more characteristic spatial parameters may be known or generally accepted values, such as standard or average values known to those skilled in the art. Alternatively, the one or more characteristic spatial parameters may be determined utilizing any system or method known to the art for determining characteristic spatial parameters of substantially crystalline materials, such as transmission electron microscopy (TEM), X-ray diffraction (XRD), scanning tunneling microscopy (STM), atomic force microscopy (AFM) and the like.

In one embodiment, a transmission electron microscopy (TEM) system may be utilized to acquire one or more crystal lattice images of the substantially crystalline material 102. Those skilled in the art will recognize that a high resolution transmission electron microscopy (HRTEM) system operating in phase contrast mode may be used to acquire images of a crystal lattice. It is further noted that utilizing a HRTEM system lattice plane spacing of approximately 1 to 10 Å are discernible.

An acquired crystal lattice image may be utilized to determine the one or more characteristic spatial parameters, such as the one or more lattice plane spacings, of the substantially crystalline material 102. A computing system communicatively coupled to the TEM system may be configured to determine the one or more characteristic spatial parameters of the substantially crystalline material 102 utilizing information associated with the TEM image acquired from the TEM system. For example, the computing system may be configured to calculate the one or more lattice plane spacings of the substantially crystalline material 102 in one or more directions utilizing the one or more acquired TEM images. It is further contemplated that the one or more characteristic spatial parameters of the substantially crystalline material 102 may be obtained utilizing other systems or methods known to the art such as X-ray diffraction and the like.

The plurality of standard particles 104 may be disposed proximate to the substantially crystalline material 102 in order to allow for spatial comparison between them. The one or more spatial parameters of the standard particles 104 may be determined utilizing a spatial relationship between the standard particles 104 and the crystal structure of the substantially crystalline material 102. For example, the one or more spatial parameters of the standard particles 104 may be determined by correlating the one or more spatial parameters to a quantity or amount of identifiable crystal features of the substantially crystalline material 102, such as crystal lattices, lattice planes, unit cells, and the like. In one embodiment the identifiable crystal features may be discretely counted to determine the quantity of identifiable crystal features corresponding to the one or more spatial parameters of at least some of standard particles 104. The one or more spatial parameters of the standard particles 104 may be determined utilizing the quantity or amount of identifiable crystal features and the one or more characteristic spatial parameters of the substantially crystalline material 102 associated with the identifiable crystal features. For example, the quantity of identifiable crystal features associated with the one or more spatial parameters of the standard particles 104 may be converted to one or more measurement values in the same fundamental unit system (e.g. International System of Units "SI") as the one or more characteristic spatial parameters of the substantially crystalline material 102 utilizing measurement values of the one or more characteristic spatial parameters associated with the identifiable crystal features.

The system 100 may further include a microscopy system 106 configured to acquire imagery data associated with the spatial relationship between the standard particles 104 and at least a portion of the substantially crystalline material 102 disposed on the sample stage 105. The microscopy system may include any system capable of acquiring imagery data from a sample at a sufficient resolution level to identify one or more crystal features of the substantially crystalline material 102. TEM systems are described generally in David B. Williams, C. Barry Carter, Transmission Electron Microscopy, Second Edition, Springer (2009), which is incorporated herein by reference.

FIG. 1C depicts an embodiment of the imagery data that may be acquired by the microscopy system 106, wherein silica particles disposed proximate to asbestos are imaged by a TEM system. It is contemplated that any variety and combination of standard particles and substantially crystalline materials may be used without departing from the essence of the present invention. Accordingly, the embodiment illustrated by FIG. 1C is only included by way of example and not intended to limit the present invention in any way.

The system 100 may further include a computing system 108 communicatively coupled to the microscopy system 106. The computing system 108 may be configured to receive imagery data associated with the one or more standard particles 104 and at least a portion of the substantially crystalline material 102. In one embodiment, the computing system 108 may include a carrier medium 110 such as a flash, solid-state, optical, random access or other static or dynamic memory device configured with program instructions 112 including a measurement algorithm 114. The measurement algorithm 114 may include an algorithm for determining the one or more spatial parameters of the standard particles 104 utilizing imagery data acquired by the microscopy system 106. The measurement algorithm 114 may include instructions directing the computing system 108 to establish a spatial relationship between the plurality of standard particles 104 and the substantially crystalline material utilizing the acquired imagery data. For example, the established spatial relationship may be associated with the quantity or amount of identifiable crystal features of the substantially crystalline material 102 corresponding to the one or more spatial parameters of the plurality of standard particles 104. The measurement algorithm 114 may further include instructions directing the computing system 108 to determine the one or more measurement values of the one or more spatial parameters of the standard particles 104 utilizing the one or more characteristic spatial parameters of the substantially crystalline material 102 associated with the identifiable crystal features.

The one or more characteristic spatial parameters of the substantially crystalline material 102 may include a selected value such as the known lattice plane spacings of the substantially crystalline material (e.g. gold). Alternatively the one or more characteristic spatial parameters of the substantially crystalline material 102 may include approximations or standard values known in the art. In one embodiment, the one or more characteristic spatial parameters of the substantially crystalline material 102 may be determined utilizing a system or method known in the art. For example, the computing system 108 may be configured to determine the one or more characteristic spatial parameters of the substantially crystalline material 102 utilizing information associated with a TEM image acquired from the microscopy system 106.

It is further contemplated that in one embodiment of the system 100, the standard particles 104 may include the substantially crystalline material 102. Accordingly, the computing system 108 may be configured to determine the one or more spatial parameters of the standard particles 104 utilizing a TEM image of one or more of the standard particles 104 acquired from the microscopy system 106 in the same manner (previously discussed) as that utilized to determine the one or more characteristic spatial parameters of the substantially crystalline material 102.

Figure 2:
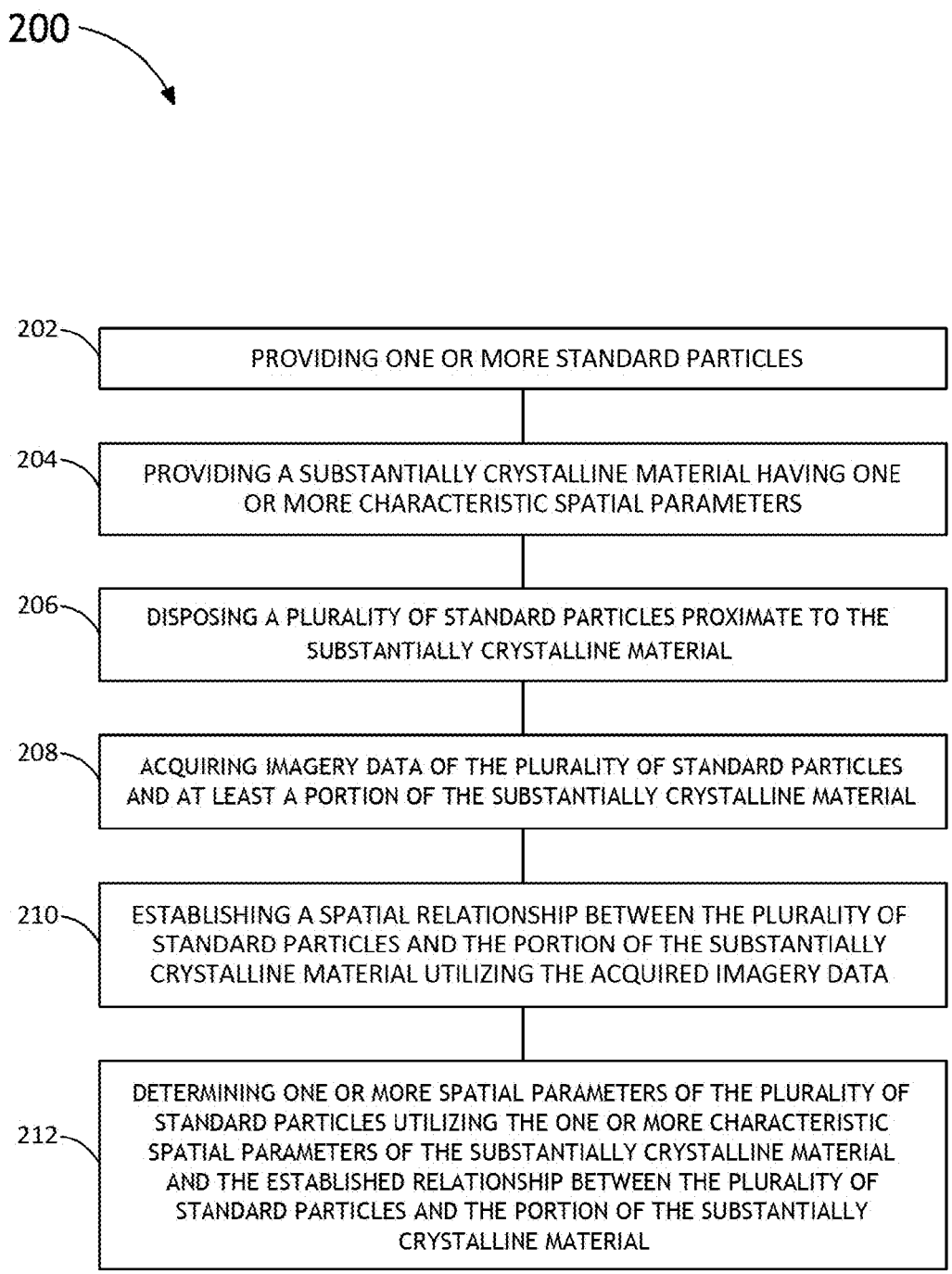
FIG. 2 is a flow diagram illustrating a method for determining one or more spatial parameters of a plurality of standard particles, in accordance with one embodiment of the present invention.

In accordance with the foregoing system 100, FIG. 2 illustrates a method 200 for determining the one or more spatial parameters of the one or more standard particles 104 utilizing a spatial comparison between the one or more standard particles 104 and a substantially crystalline material 102. The method 200 may include one or more of the following steps: (i) step 202, providing a plurality of standard particles 104, (ii) step 204, providing the substantially crystalline 102 material having the one or more characteristic spatial parameters, (iii) step 206, disposing the plurality of standard particles 104 proximate to the substantially crystalline material 102, (iv) step 208, acquiring imagery data of the plurality of standard particles 104 and at least a portion of the substantially crystalline material 102, (v) step 210, establishing a spatial relationship between the plurality of standard particles 104 and the portion of the substantially crystalline material 102 utilizing the acquired imagery data, and (vi) step 212, determining the one or more spatial parameters of the plurality of standard particles 104 utilizing the one or more characteristic spatial parameters of the substantially crystalline material 102 and the established relationship between the plurality of standard particles 104 and the portion of the substantially crystalline material 102.

In steps 202, 204, and 206 the plurality of standard particles 104 may be disposed proximate to the substantially crystalline material 102 in any manner that allows the microscopy system 106 to acquire imagery data of the plurality of standard particles 104 and the substantially crystalline material 102. For example, the plurality of standard particles 104 may be disposed on top of the substantially crystalline material 102 or substantially adjacent to the substantially crystalline material 102. The foregoing arrangements of the plurality of standard particles 104 and the substantially crystalline material 102 are included by way of example only and are not intended to limit the present invention in any way. Any arrangement that allows for the acquisition of imagery data of the plurality of standard particles 104 and the portion of the substantially crystalline material 102 may be acceptable.

In step 208, imagery data of the plurality of standard particles 104 and the substantially crystalline material 102 may be acquired utilizing the microscopy system 106 or any system or device configured to acquire data associated with the spatial relationship between the plurality of standard particles 104 and the identifiable crystal features of the substantially crystalline material 102. In step 210, the spatial relationship between the plurality of standard particles 104 and the substantially crystalline material 102 may be established by determining the quantity or amount of identifiable crystal features of the substantially crystalline material 102 associated with the one or more spatial parameters of the plurality of standard particles 104. For example, the one or more spatial parameters of the plurality of standard particles 104 may be associated with the quantity of identifiable crystal features of the substantially crystalline material 102.

In step 210, the one or more spatial parameters of the plurality of standard particles 104 may be determined by converting the quantity or amount of identifiable crystal features associated with the one or more spatial parameters of the plurality of standard particles 104 to the one or more measurement values of the one or more spatial parameters utilizing the one or more characteristic parameters of the substantially crystalline material 102. Accordingly, the one or more spatial parameters of the plurality of standard particles 104 may be represented utilizing the same number system (e.g. SI) that is used to represent the one or more characteristic parameters of the substantially crystalline material 102. It is further contemplated that, the one or more spatial parameters of the plurality of standard particles 104 may be further represented utilizing alternative number systems through conversion methods known in the art.

In a further embodiment, the method 200 may include an additional step of determining a second set of one or more spatial parameters of a second set of plurality of standard particles utilizing the one or more spatial parameters determined for the first set of the plurality of standard particles 104. It is contemplated that the plurality of standard particles 104 having a determined set of one or more spatial parameters may be utilized to measure any other particle, object, material, artifact, and the like. For example, the one or more spatial parameters of the second set of plurality of standard particles may be measured through extrapolation or interpolation techniques, among others known in the art.

Figure 3:
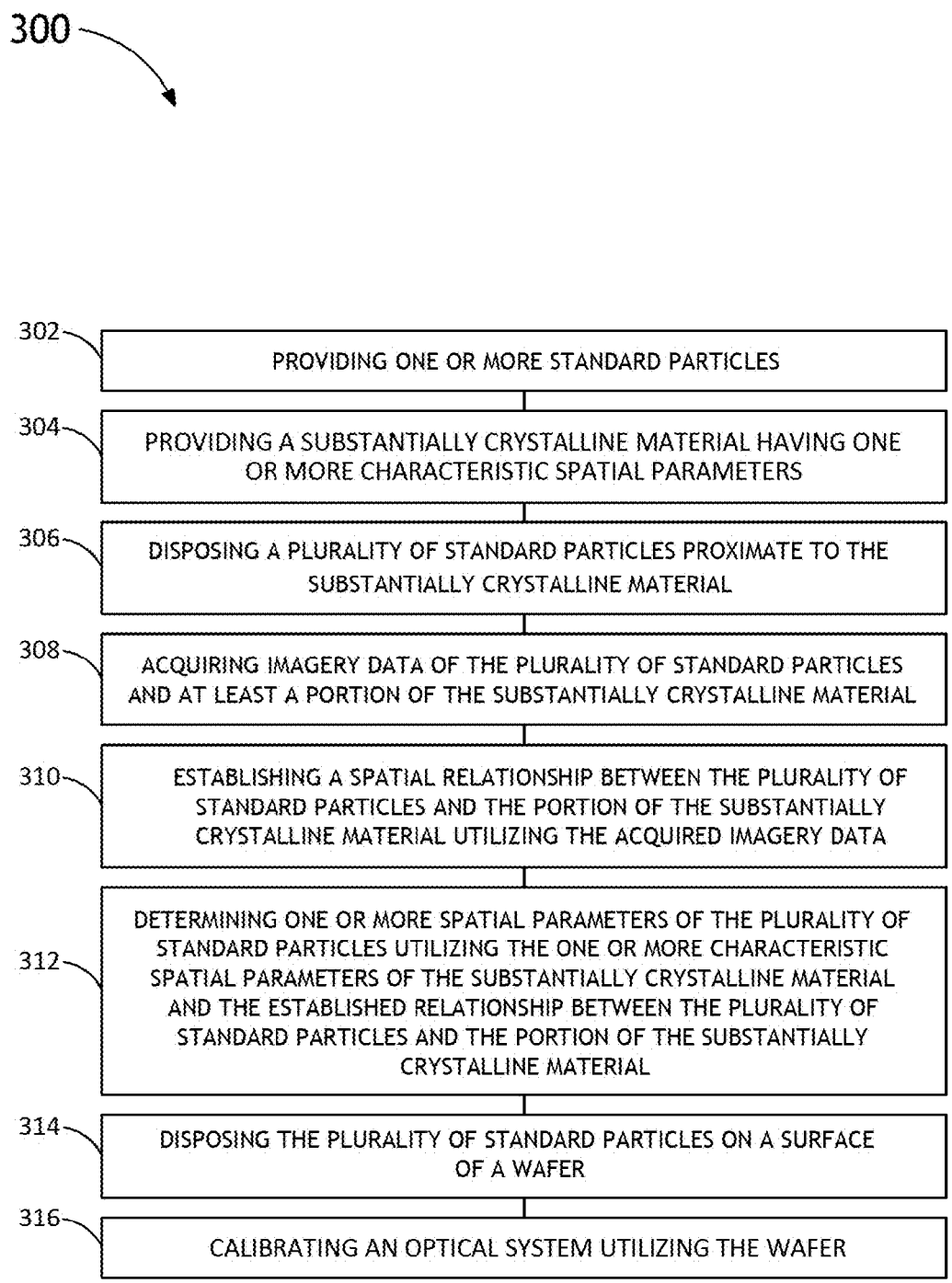
FIG. 3 is a flow diagram illustrating a method for determining one or more spatial parameters of a plurality of standard particles and for calibrating an optical system utilizing a wafer having the plurality of standard particles disposed on a surface of the wafer, in accordance with one embodiment of the present invention.

FIG. 3 illustrates a method 300 for determining the one or more spatial parameters of the plurality of standard particles 104 utilizing a spatial comparison between the plurality of standard particles 104 and a substantially crystalline material 102 and for calibrating an optical measurement system utilizing a calibration wafer having the plurality of standard particles 104 disposed on a surface of the wafer. The method 300 may include one or more of the following steps: (i) step 302, providing the plurality of standard particles 104, (ii) step 304, providing the substantially crystalline 102 material having the one or more characteristic spatial parameters, (iii) step 306, disposing the plurality of standard particles 104 proximate to the substantially crystalline material 102, (iv) step 308, acquiring imagery data of the plurality of standard particles 104 and at least a portion of the substantially crystalline material 102, (v) step 310, establishing a spatial relationship between the plurality of standard particles 104 and the portion of the substantially crystalline material 102 utilizing the acquired imagery data, (vi) step 312, determining the one or more spatial parameters of the plurality of standard particles 104 utilizing the one or more characteristic spatial parameters of the substantially crystalline material 102 and the established relationship between the plurality of standard particles 104 and the portion of the substantially crystalline material 102, (vii) step 314, disposing the plurality of standard particles 104 on the surface of a wafer, and (viii) step 316, calibrating an inspection system utilizing the wafer.

In steps 302, 304, and 306 the plurality of standard particles 104 may be disposed proximate to the substantially crystalline material 102 in any manner that allows the microscopy system 106 to acquire imagery data of the plurality of standard particles 104 and the substantially crystalline material 102. For example, the plurality of standard particles 104 may be disposed on top of the substantially crystalline material 102 or substantially adjacent to the substantially crystalline material 102. The foregoing arrangements of the plurality of standard particles 104 and the substantially crystalline material 102 are included by way of example only and are not intended to limit the present invention in any way. Any arrangement that allows for the acquisition of imagery data of the plurality of standard particles 104 and the portion of the substantially crystalline material 102 may be acceptable.

In step 308, imagery data of the plurality of standard particles 104 and the substantially crystalline material 102 may be acquired utilizing the microscopy system 106 or any system or device configured to acquire data associated with the spatial relationship between the plurality of standard particles 104 and the identifiable crystal features of the substantially crystalline material 102. In step 310, the spatial relationship between the plurality of standard particles 104 and the substantially crystalline material 102 may be established by determining the quantity or amount of identifiable crystal features of the substantially crystalline material 102 associated with the one or more spatial parameters of the plurality of standard particles 104. For example, the one or more spatial parameters of the plurality of standard particles 104 may be associated with the quantity of identifiable crystal features of the substantially crystalline material 102.

In step 310, the one or more spatial parameters of the plurality of standard particles 104 may be determined by converting the quantity or amount of identifiable crystal features associated with the one or more spatial parameters of the plurality of standard particles 104 to the one or more measurement values of the one or more spatial parameters utilizing the one or more characteristic parameters of the substantially crystalline material 102. Accordingly, the one or more spatial parameters of the plurality of standard particles 104 may be represented utilizing the same number system (e.g. SI) that is used to represent the one or more characteristic parameters of the substantially crystalline material 102. It is further contemplated that, the one or more spatial parameters of the plurality of standard particles 104 may be further represented utilizing alternative number systems through conversion methods known to the art.

In step 314, the plurality of standard particles 104 may be disposed on the surface of the wafer utilizing any suitable method known to the art, including but not limited to aerosol deposition or directly from colloidal liquid. In step 316, the wafer having the plurality of standard particles disposed thereon may be utilized to calibrate the optical measurement system (e.g., scattering inspection system, reflective inspection system, or metrology). In a further aspect of step 316, the optical system may acquire imagery or other optical data associated with the plurality of standard particles 104 disposed on the surface of the wafer. Further, the optical system may establish a relationship between the acquired imagery or other optical data associated with the plurality of standard particles 104 and the one or more spatial parameters of the plurality of standard particles 104. In another aspect of step 316, the optical system may utilize the established relationship between the acquired imagery data and the one or more spatial parameters of the plurality of standard particles 104 to calibrate the optical system. For example, the acquired imagery data may include one or more measured spatial parameters. The one or more measured spatial parameters may be compared against the one or more spatial parameters of the plurality of standard particles 104 to calibrate the optical system so that the one or more measured spatial parameters are substantially equal to the one or more spatial parameters of the plurality of standard particles 104.

Figure 4:
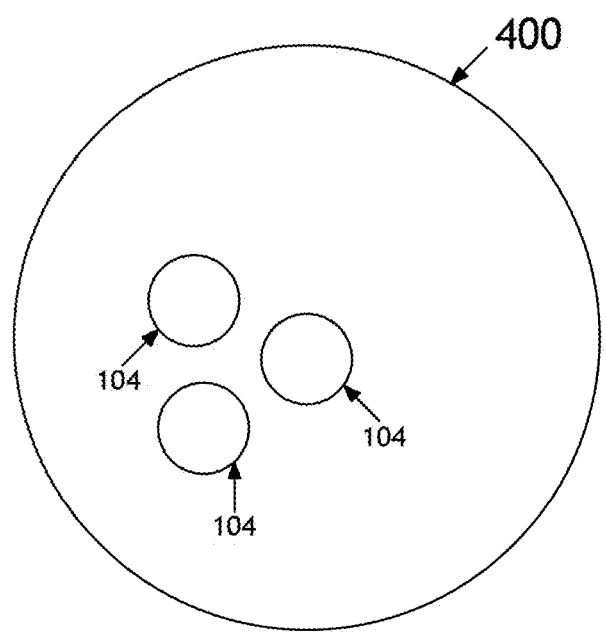
FIG. 4 illustrates a conceptual view of a wafer having a plurality of standard particles disposed on a surface of the wafer, in accordance with one embodiment of the present invention.

Referring to FIG. 4, a calibration wafer 400 configured to calibrate an inspection or metrology system may have a plurality of calibrated standard particles 104 disposed on a surface of the calibration wafer 400. The calibrated standard particles may include standard particles 104 selected from a plurality of standard particles having one or more verified spatial parameters. The one or more verified spatial parameters may include the one or more spatial parameters of the plurality of standard particles 104 measured and/or confirmed utilizing a spatial comparison between the plurality of standard particles 104 and the substantially crystalline material, as previously discussed herein.

Figure 5:
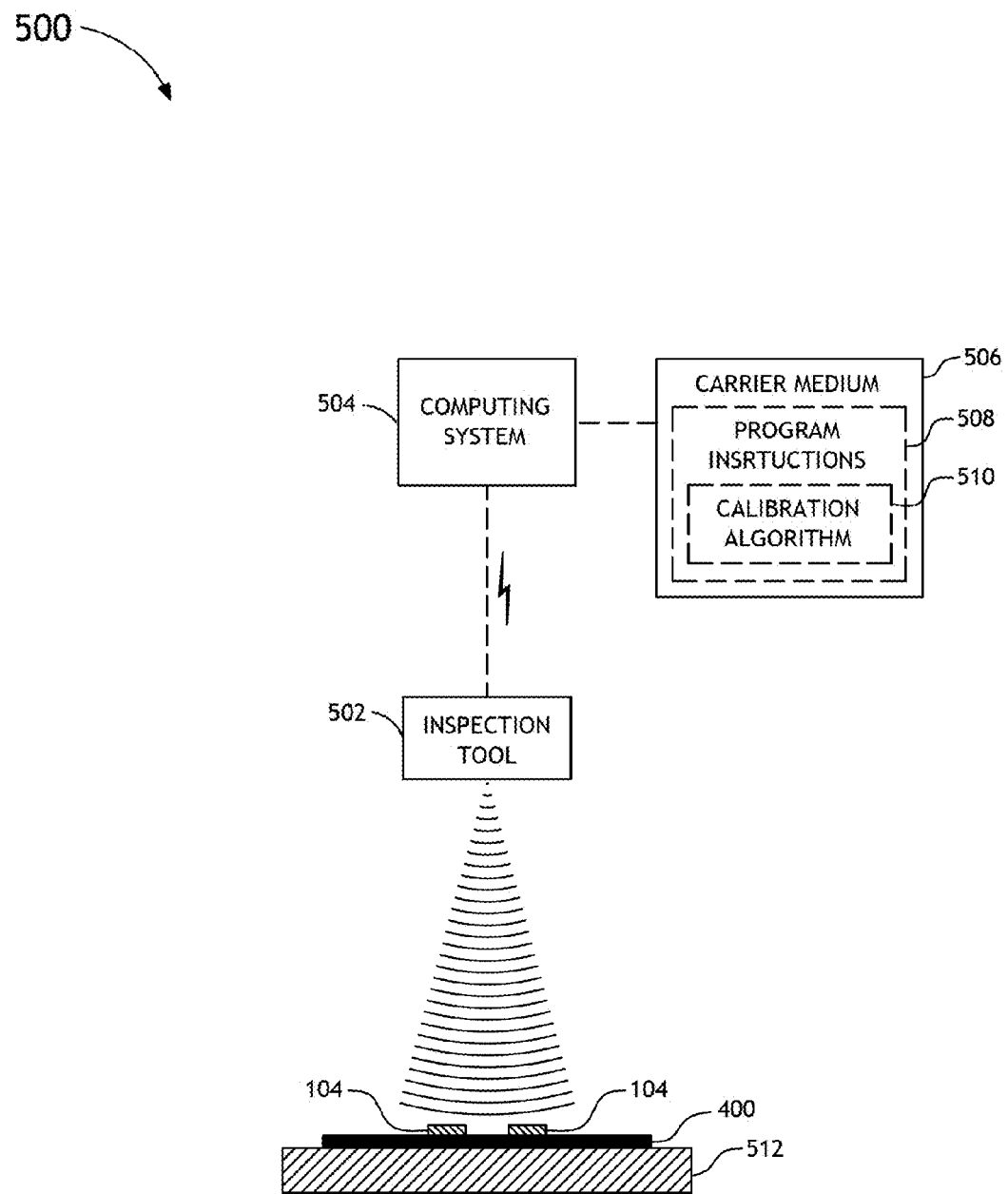
FIG. 5 illustrates an optical system configured for calibration utilizing a wafer having a plurality of standard particles disposed on a surface of the wafer, in accordance with one embodiment of the present invention.

FIG. 5 illustrates an optical measurement system 500 configured to measure or analyze defects of one or more sample, such as a photomask, wafer, or any other sample that may be analyzed utilizing an optical inspection system. The optical measurement system 500 may include an inspection system or a metrology system. The optical measurement system 500 may be further configured to be calibrated with the calibration wafer 400 having the plurality of standard particles 104 disposed on the surface of the calibration wafer 400. The optical measurement system 500 may include a measurement tool 502 (e.g., scattering based inspection tool, reflective based inspection tool, or metrology tool) having an illumination source configured to direct illumination to the surface of the calibration wafer 400. The optical measurement system 500 may further include a sample stage 512 configured to hold the calibration wafer 400 during the calibration process. The sample stage 512 may be configured to hold the calibration wafer in a location where the calibration wafer 400 may receive at least a portion of illumination transmitted from the illumination source of the measurement tool 502. The sample stage 512 may be further configured to actuate the calibration wafer 400 to a user selected location. In a further embodiment, the sample stage 512 may be configured to rotate the sample during a measurement process. The sample stage 512 may further be communicatively coupled to one or more computing systems 504 and configured to actuate the calibration wafer 400 to the user selected location or to a location determined by the computing system 504.

The optical measurement system 500 may further include a detector (not shown) configured to directly or indirectly receive at least a portion of illumination scattered from the surface of the calibration wafer 400. The detector may be any suitable detector known to the art, such as a photomultiplier tube for analyzing or measuring characteristics of illumination scattered from the surface of the calibration wafer 400 (e.g. amplitude, intensity, phase, polarity, frequency, wavelength, and the like). The system 500 may further include one or more computing systems 504 communicatively coupled to the detector. The computing system 504 may be configured to receive information regarding characteristics of illumination scattered from the surface of the calibration wafer 400 from the detector. The computing system 504 may be further configured to execute a calibration algorithm 510 from program instructions 508 on a carrier medium 506. The calibration algorithm 510 may be any calibration algorithm known to the art for calibrating an optical measurement system (e.g., inspection system or metrology system) utilizing imagery or other optical data associated with the plurality of standard particles 104 of the calibration wafer 400, wherein the imagery or other optical data may be acquired from illumination acquired from the surface of the calibration wafer 400 received by the detector. For example, the calibration algorithm may include the steps of: (i) acquiring imagery or other optical data associated with the plurality of standard particles 104 disposed on the surface of the calibration wafer 400, (ii) establishing a relationship between the acquired imagery or other optical data and the one or more spatial parameters of the plurality of standard particles 104, and (iii) calibrating the inspection system utilizing the established relationship between the acquired imagery or other optical data associated with the plurality of standard particles 104 and the one or more spatial parameters of the plurality of standard particles 104.

The optical measurement system 500 may include one or more illumination optical elements (e.g. retarders, quarter wave plates, focus optics, phase modulators, polarizers, mirrors, beam splitters, reflectors, converging/diverging lenses, prisms, etc.) positioned between the illumination source (not shown) and the surface of the wafer 400. The illumination optical elements may be configured to directly or indirectly receive illumination emanating from the illumination source of the measurement tool 502. The illumination optical elements may be further configured to transmit at least a portion of illumination directly or indirectly received from the illumination source along an illumination path of the inspection system 500 to the surface of the calibration wafer 400. The illumination path may be any path along which illumination can travel from the illumination source of the measurement tool 502 to the surface of the calibration wafer 400, such as a direct line of sight between the illumination source and the surface of the calibration wafer 400. In some embodiments, the illumination path may be a path delineated by a configuration of one or more optical elements including, but not limited to, the illumination optical elements or any other optical elements disclosed herein.

In one embodiment the optical measurement system 500 may include collection optical elements (e.g. retarders, quarter wave plates, focus optics, phase modulators, filters, polarizers, mirrors, beam splitters, reflectors, converging/diverging lenses, prisms, etc.) configured to directly or indirectly receive at least a portion of illumination scattered from the surface of the calibration wafer 400. The collection optical elements may be further configured to transmit at least a portion of illumination directly or indirectly received from the surface of the calibration wafer 400 along a collection path of the optical measurement system 500 to the detector of the measurement tool 502. The collection path may be any path along which illumination can travel from the surface of the calibration wafer 400 to the detector. In some embodiments, the collection path may be a path delineated by a configuration of one or more optical elements including, but not limited to, the collection optical elements or any other optical elements disclosed herein.

It is contemplated that the inventive aspects of the optical measurement system 500 may be extended to a wide array of inspection or metrology systems utilized in the fabrication or analysis of semiconductors or semiconductor components. The optical measurement system 500 may be configured for one or more modes of operation known in the art. For example, the optical measurement system 500 may be configured for bright-field inspection, dark-field inspection, or any other mode or configuration now or hereafter known to the art. The optical measurement system 500 may be further configured for one or more inspection capabilities known to the art. For example, the optical measurement system 500 may be configured for inspecting one or more photomasks, patterned wafers, unpatterned wafers, or any other inspection capability now or hereafter known to the art.

It should be recognized that the various steps described throughout the present disclosure may be carried out by a single computing system or, alternatively, a multiple computing system. Moreover, different subsystems of the system may include a computing system suitable for carrying out at least a portion of the steps described above. Therefore, the above description should not be interpreted as a limitation on the present invention but merely an illustration. Further, the one or more computing systems may be configured to perform any other step(s) of any of the method embodiments described herein.

The computing system may include, but is not limited to, a personal computing system, mainframe computing system, workstation, image computer, parallel processor, or any other device known in the art. In general, the term "computing system" may be broadly defined to encompass any device having one or more processors, which execute instructions from a memory medium.

Program instructions implementing methods such as those described herein may be transmitted over or stored on carrier medium. The carrier medium may be a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A system for determining one or more spatial parameters of a plurality of standard particles, comprising:
a substantially crystalline material including a crystal structure having one or more identifiable crystal features, the one or more identifiable crystal features including at least one of a crystal lattice, a unit cell of the crystal structure, or a spacing between crystal lattice planes of the crystal structure;
a plurality of standard particles disposed proximate to a portion of the substantially crystalline material, the substantially crystalline material and the plurality of standard particles arranged for spatial comparison between the crystal structure of the substantially crystalline material and the plurality of standard particles;
a microscopy system configured to simultaneously acquire imagery data of the plurality of standard particles and imagery data of the one or more identifiable crystal features of the portion of the substantially crystalline material; and
a computing system communicatively coupled to the microscopy system, the computing system configured to establish a spatial relationship between the plurality of standard particles and the crystal structure of the portion of the substantially crystalline material, the computing system further configured to determine one or more calibrated spatial parameters of the plurality of standard particles by comparing the one or more identifiable crystal features of the crystal structure of the substantially crystalline material to the one or more spatial parameters of the plurality of standard particles.

2. The system of claim 1, wherein the one or more spatial parameters of the plurality of standard particles comprise:
one or more statistical parameters associated with the plurality of standard particles.

3. The system of claim 2, wherein the one or more statistical parameters comprise:
at least one of an average size, a median size, a most probable size, or a standard deviation in size.

4. The system of claim 1, wherein the microscopy system comprises a transmission electron microscopy (TEM) system.

5. The system of claim 1, wherein the computing system is further configured to determine the one or more characteristic spatial parameters of the substantially crystalline material utilizing an image acquired by the microscopy system.

6. The system of claim 1, wherein the substantially crystalline material comprises a monocrystalline material.

7. The system of claim 1, wherein the substantially crystalline material comprises at least one of silicon, gold, or asbestos.

8. The system of claim 1, wherein one or more of the plurality of standard particles comprise a plurality of silica particles.

9. The system of claim 1, wherein one or more of the plurality of standard particles are formed from one or more substantially crystalline materials.

10. A system for determining one or more spatial parameters of one or more standard particles, comprising:
a substantially crystalline material including a crystal structure having one or more identifiable crystal features, the one or more identifiable crystal features including at least one of a crystal lattice, a unit cell of the crystal structure, or a spacing between crystal lattice planes of the crystal structure;
one or more standard particles disposed proximate to a portion of the substantially crystalline material, the substantially crystalline material and the one or more standard particles arranged for spatial comparison between the crystal structure of the substantially crystalline material and the one or more standard particles;
a microscopy system configured to simultaneously acquire imagery data of the one or more standard particles and imagery data of the one or more identifiable crystal features of the portion of the substantially crystalline material; and
a computing system communicatively coupled to the microscopy system, the computing system configured to establish a spatial relationship between the one or more standard particles and the crystal structure of the portion of the substantially crystalline material, the computing system further configured to determine one or more calibrated spatial parameters of the one or more standard particles by comparing the one or more identifiable crystal features of the crystal structure of the substantially crystalline material to the one or more spatial parameters of the plurality of standard particles.

11. The system of claim 10, wherein the one or more spatial parameters of the one or more standard particles comprises a size of the standard particles.

12. A method for determining one or more spatial parameters of a plurality of standard particles, comprising:
providing a plurality of standard particles;
providing a substantially crystalline material including a crystal structure having one or more identifiable crystal features, the one or more identifiable crystal features including at least one of a crystal lattice, a unit cell of the crystal structure, or a spacing between crystal lattice planes of the crystal structure;
disposing the plurality of standard particles proximate to a portion of the substantially crystalline material for spatial comparison between the crystal structure of the substantially crystalline material and the plurality of standard particles;
simultaneously acquiring imagery data of the plurality of standard particles and imagery data of the one or more identifiable crystal features of the portion of the substantially crystalline material;
establishing a spatial relationship between the plurality of standard particles and the portion of the substantially crystalline material utilizing the acquired imagery data; and determining one or more calibrated spatial parameters of the plurality of standard particles by comparing the one or more identifiable crystal features of the crystal structure of the substantially crystalline material to the one or more spatial parameters of the plurality of standard particles.

13. The method of claim 12, wherein the method further includes the step of determining one or more identifiable crystal features of the crystal structure of the substantially crystalline material utilizing an image acquired from the substantially crystalline material.

14. The method of claim 12, wherein the determining one or more calibrated spatial parameters of the plurality of standard particles by comparing the one or more identifiable crystal features of the crystal structure of the substantially crystalline material to the one or more spatial parameters of the plurality of standard particles comprises:
   determining an average size of the plurality of standard particles by comparing the one or more identifiable crystal features of the crystal structure of the substantially crystalline material to the one or more spatial parameters of the plurality of standard particles.

15. The method of claim 12, wherein the substantially crystalline material comprises at least one of silicon, gold, and asbestos.

16. The method of claim 12, wherein the method further comprises the step of determining a second set of one or more calibrated spatial parameters of a second plurality of standard particles utilizing the one or more calibrated spatial parameters of the plurality of standard particles and a spatial comparison between the plurality of standard particles and the second plurality of standard particles.

17. A method for determining one or more spatial parameters of one or more standard particles, comprising:
   providing one or more standard particles;
   providing a substantially crystalline material including a crystal structure having one or more identifiable crystal features, the one or more identifiable crystal features including at least one of a crystal lattice, a unit cell of the crystal structure, or a spacing between crystal lattice planes of the crystal structure;
   disposing the one or more standard particles proximate to a portion of the substantially crystalline material for spatial comparison between the crystal structure of the substantially crystalline material and the plurality of standard particles;
   simultaneously acquiring imagery data of the one or more standard particles and imagery data of the one or more identifiable crystal features of the portion of the substantially crystalline material;
   establishing a spatial relationship between the one or more standard particles and the portion of the substantially crystalline material utilizing the acquired imagery data; and
   determining one or more calibrated spatial parameters of the one or more standard particles by comparing the one or more identifiable crystal features of the crystal structure of the substantially crystalline material to the one or more spatial parameters of the one or more standard particles.

18. The method of claim 17, wherein the determining one or more calibrated spatial parameters of the one or more standard particles by comparing the one or more identifiable crystal features of the crystal structure of the substantially crystalline material to the one or more spatial parameters of the one or more standard particles comprises:
   determining a size of the one or more standard particles by comparing the one or more identifiable crystal features of the crystal structure of the substantially crystalline material to the one or more spatial parameters of the one or more standard particles.

19. A method for calibrating an optical measurement system utilizing a plurality of standard particles, comprising the steps of:
   providing a plurality of standard particles;
   providing a substantially crystalline material including a crystal structure having one or more identifiable crystal features, the one or more identifiable crystal features including at least one of a crystal lattice, a unit cell of the crystal structure, or a spacing between crystal lattice planes of the crystal structure;
   disposing the plurality of standard particles proximate to a portion of the substantially crystalline material for spatial comparison between the crystal structure of the substantially crystalline material and the plurality of standard particles;
   simultaneously acquiring imagery data of the plurality of standard particles and imagery data of the one or more identifiable crystal features of the portion of the substantially crystalline material;
   establishing a spatial relationship between the plurality of standard particles and the portion of the substantially crystalline material utilizing the acquired imagery data;
   determining one or more calibrated spatial parameters of the plurality of standard particles by comparing the one or more identifiable crystal features of the crystal structure of the substantially crystalline material to the one or more spatial parameters of the plurality of standard particles;
   disposing the plurality of standard particles on a surface of a wafer; and
   calibrating an optical measurement system utilizing the wafer having the plurality of standard particles disposed on the surface of the wafer by:
   acquiring optical data associated with the plurality of standard particles disposed on the surface of the wafer; and
   establishing a relationship between the acquired optical data associated with the plurality of standard particles and the one or more spatial parameters of the plurality of standard particles.

20. The method of claim 19, wherein the optical data comprises:
   at least one of imagery data or scattering data.

21. The method of claim 19, wherein the method further includes the step of determining one or more identifiable crystal features of the crystal structure of the substantially crystalline material utilizing an image acquired from at least a portion of the substantially crystalline material.

22. The method of claim 19, wherein the substantially crystalline material comprises at least one of silicon, gold, and asbestos.

23. A wafer for calibrating an optical measurement system, comprising:
   a calibration wafer; and
   plurality of calibrated standard particles disposed on a surface of the wafer, each of the plurality of calibrated standard particles selected from a plurality of standard particles having one or more verified spatial parameters, the one or more verified spatial parameters confirmed utilizing a spatial comparison between one or more standard particles of the plurality of standard particles and one or more identifiable crystal features of a crystal structure of a substantially crystalline material simultaneously imaged with a microscopy system, the one or more identifiable crystal features including at least one of a crystal lattice, a unit cell of the crystal structure, or a spacing between crystal lattice planes of the crystal structure.

24. The wafer of claim 23, wherein some of the plurality of calibrated standard particles are formed from one or more substantially crystalline materials.

25. An optical measurement system configured to perform optical inspection or optical metrology on one or more wafers, comprising:

an illumination source configured to direct illumination to a surface of a sample disposed on a sample stage;

a sample stage configured to receive a calibration wafer, the calibration wafer having a plurality of calibrated standard particles disposed on a surface of the calibration wafer, the plurality of calibrated standard particles selected from a plurality of standard particles having one or more verified spatial parameters, the one or more verified spatial parameters confirmed utilizing a spatial comparison between one or more standard particles of the plurality of standard particles and one or more identifiable crystal features of a crystal structure of a substantially crystalline material simultaneously imaged with a microscopy system, the one or more identifiable crystal features including at least one of a crystal lattice, a unit cell of the crystal structure, or a spacing between crystal lattice planes of the crystal structure;

a detector configured to receive illumination from the surface of the sample; and a computing system communicatively coupled to the detector, the computing system configured to acquire information associated with illumination received by the detector, the computing system further configured to acquire data associated with the plurality of calibrated standard particles disposed on the surface of the calibration wafer utilizing information associated with illumination received by the detector, the computing system further configured to establish a relationship between the plurality of calibrated standard particles disposed on the surface of the wafer and the one or more verified spatial parameters of the plurality of calibrated standard particles, wherein the computing system is further configured to calibrate subsequent measurements made by the inspection system utilizing the established relationship.

* * * * *